United States Patent [19]

Gabriele et al.

[11] Patent Number: 4,552,885

[45] Date of Patent: Nov. 12, 1985

[54] STABILIZED FUNGICIDE COMPOSITIONS

[75] Inventors: Peter D. Gabriele, Danbury, Conn.; Jerry E. Rademan, Pearl River, N.Y.

[73] Assignee: Ciba Geigy Corporation, Ardsley, N.Y.

[21] Appl. No.: 451,185

[22] Filed: Dec. 22, 1982

Related U.S. Application Data

[63] Continuation-in-part of Ser. No. 334,197, Dec. 24, 1981, abandoned.

[51] Int. Cl.$^4$ .................... A61K 31/445; A01N 43/40
[52] U.S. Cl. ..................................... 514/316; 514/315
[58] Field of Search ........................ 260/45.8; 424/174

[56] References Cited

U.S. PATENT DOCUMENTS

| | | | |
|---|---|---|---|
| 3,393,990 | 7/1968 | Geary | 71/65 |
| 4,045,555 | 8/1977 | Ferrari et al. | 424/174 |
| 4,110,304 | 8/1978 | Glig et al. | 260/45.8 |
| 4,265,805 | 5/1981 | Thomas | 260/45.8 |
| 4,276,211 | 6/1981 | Singer et al. | 260/29.6 |
| 4,283,327 | 8/1981 | Dexter et al. | 260/45.8 |

FOREIGN PATENT DOCUMENTS

| | | | |
|---|---|---|---|
| 2753 | 7/1979 | European Pat. Off. | 260/29.6 |
| 068643 | 11/1982 | Japan | 260/29.6 |

*Primary Examiner*—Elbert L. Roberts
*Attorney, Agent, or Firm*—Harry Falber

[57] ABSTRACT

Fungicides and fungicidal formulations are stabilized against the adverse effects of exposure to light by the addition thereto of effective amounts of a 2,2,6,6-tetraalkylpiperidine compound, or a UV absorber, or a blend of said piperidine compound and said UV absorber.

26 Claims, No Drawings

STABILIZED FUNGICIDE COMPOSITIONS

RELATED APPLICATION

This application is a continuation-in-part of application Ser. No. 334,197, filed Dec. 24, 1981 now abandoned.

The use of organic fungicides for the protection of natural and synthetic organic materials from microbiological attack in exterior service application is wide spread. All organic materials are potential carbon sources for biological assimilation. Fungicides are used extensively in agricultural, chemical and polymer technology to protect organics which are either indigenous to the outdoors or require an extended exterior service life. Failure of a fungicide to perform properly results in microbiological invasion. Microorganisms deface and destroy organic substances through enzymatic attack. The role of the fungicide is to create a toxic environment which is not conducive to supporting life. A toxic environment must be maintained for organic materials in exterior service situations to remain free from biota.

Most organic fungicides are sensitive to sunlight and readily decompose upon exposure. Many organic and organo metallic fungicides are strong UV absorbing chemicals with one or more photo-sensitive bonds. Photochemical decomposition of fungicides has been detailed in the literature. Photodecomposition of a fungicide is the primary factor in reducing the effective service life of a fungicide. Fungicides are presently being formulated to take into account migration and loss of fungicide due to natural weathering. The efficiency of a fungicide therefore depends upon the maintenance of a minimum inhibitory concentration (MIC) of a fungicide for a precise period of time. This is referred to as the efficacy of a system.

The minimum inhibitory concentration is complemented by the concept of "shaped-charge" Horsfall, "Principles of Fungicidal Action" Chronica Botanica Mass. (1956) A fungicide is active only if the original molecular design of the fungicide is maintained when in contact with the invading organism. The concept of "shaped-charge" states that the fungicide molecule has at least two sites which must be maintained for effective fungicidal activity. One site facilities fungicide passage through the organism cell wall. The other site the toxaphor or poison center, delivers the actual lethal chemistry to the organism. These sites must be maintained in order for the fungicide to be effective. Photochemical decomposition destroys these important sites and thus the shape charge leaving the fungicide ineffective.

Photochemical decomposition not only reduces the fungicide's efficiency through destruction of shape charge but may also produce volatile by-products of decomposition that eventually produce even more toxic materials. The latter two situations pose both an environmental as well as a health hazard. It is therefore desirable to reduce or prevent fungicides from the degradation produced by exposure to ultra-violet sources. Additional background information on fungicide stabilization may be obtained from Enninga et al, "Fungicides in Latex Paints", *Biodeterioration of Materials,* Proceedings of 1st International Biodeterioration Symposium, Elsevier Publishing Co., New York, pp. 326–332 (1968).

Two methods have generally been utilized to overcome this breakdown problem. A first approach involves loading high levels of fungicide into the formulation in order to compensate for the breakdown over time. This approach is further discussed in the Enninga et al paper. The second approach involves the incorporation of a screen to physically block the sun's harmful UV radiation. The disadvantages of the first approach are two-fold. High levels of fungicide are costly. High levels are also a danger to mammalian contact. Therefore, the high loading of a fungicide beyond the MIC is economically and environmentally undesirable. The primary disadvantage of the second approach is that UV screens are usually pigments. The disadvantages of the use of pigments include poor solubility, chalking, opacity and embrittlement. Pigments also tend to initiate photodecomposition. Accordingly, this second approach is likewise deemed inadequate.

The present invention relates therefore to the stabilization of fungicides against light induced deterioration by the incorporation in fungicide compositions of a 2,2,6,6-tetraalkylpiperidine compound, or a UV absorber, or preferably a blend thereof, said blends providing enhanced protection. The invention also relates to the stabilized compositions resulting therefrom as well as to formulated systems, such as paints, substrate treatments and protective coatings, containing said stabilized fungicides.

The utilization of such stabilizer systems substantially overcomes most of the difficulties encountered with prior art approaches. Thus, the chemical mechanisms and solubility characteristics of these compounds facilitates their incorporation into fungicide compositions and their ability to prevent deterioration of the fungicide and consequent reduction in fungicidal activity. More specifically, the UV absorber serves to prevent the fungicide from "seeing" the ultraviolet light which causes its degradation. In turn, the piperidine compound prevents the fungicide from degrading due to free radical attack on the molecule. The compound terminates these available free radicals. The combination of the two therefore provides added benefits by attacking two distinct mechanisms of degradation of the fungicide. Of primary significance, the stabilization effectiveness of these systems allows for a reduction in the concentration levels necessary to provide a satisfactory fungicidal response. Accordingly, the environmental and economic disadvantages noted hereinabove are now substantially eliminated.

The individual piperdine compounds and UV absorbers as well as the combination thereof are known and are recognized for their ability to combat light-induced degradation of polymeric substrates and various resin-based coatings. Representative patents disclosing the individual piperidines and UV absorbers are noted hereinbelow. Blends for stabilization of said substrates and coatings are diclosed, for example, in U.S. Pat. Nos. 4,110,304 4,283,327, 4,324,933, 4,344,876 and European Pat. No. 2,753.

The use of individual UV absorbers to combat light-induced degradation of insecticides is likewise known. For example, U.S. Pat. No. 4,056,610 and U.S. Pat. No. 4,171,355 disclose the use of UV absorbers such as benzophenones, benzotriazoles, malonates, triazines and nickel compounds to stabilize pyrethroid insecticides. Ger. Offen. No. 2,139,625 discloses the use of specific benzotriazoles for the stabilization of ethylphenoxyepoxy-octene insecticides. South African No. 71/05,370 likewise discloses the use of specific benzotriazoles to stabilize larvacides. Chem. Abstracts No.

77/18322 discloses the use of benzophenones for the stabilization of pyrethrin and allethrin insecticides.

The stabilization of fungicidal compositions, however, represents a special situation in view of the unique problems encountered therewith, said problems being itemized hereinabove. Accordingly, the unexpected discovery discussed and claimed herein reflects an understanding of these problems and a recognition of the elements that distinguish the stabilization of fungicides from the stabilization of various polymeric substrates, coatings and insecticides.

The 2,2,6,6-tetraalkylpiperidine compounds to be used according to the invention are generally known and are recognized for their ability to combat light degradation. U.S. Pat. Nos. 3,542,729, 3,640,928, 3,840,494, 4,021,432, 4,049,647, 4.064,102, 4,086,204 and 4,265,805 are typical of the numerous patents that disclose such piperidine light stabilizers.

The hindered amine light stabilizers useful in the instant invention are in particular 2,2,6,6-tetraalkylpiperidine compounds which contain a group of the formula (I)

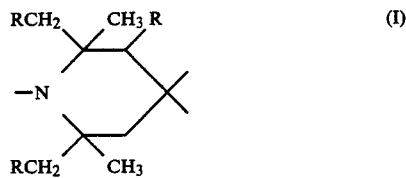

in which R is hydrogen or methyl.

The light stabilisers to be used according to the invention include in particular the following classes of compounds:

(a) Light stabilisers of the formula (II)

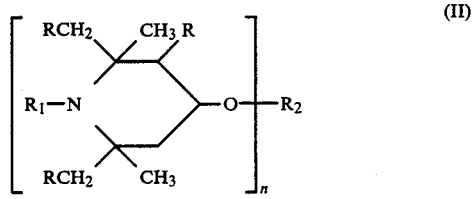

in which n is a number from 1-4 inclusive, preferably 1 or 2; R is as defined under the formula (I); $R_1$ is hydrogen, oxyl, $C_1$–$C_{18}$ alkyl, $C_3$–$C_8$ alkenyl, $C_3$–$C_8$ alkynyl, $C_7$–$C_{12}$ aralkyl, $C_1$–$C_8$ alkanoyl, $C_3$–$C_5$ alkenoyl, glycidyl, a group —$CH_2CH(OH)$—Z wherein Z is hydrogen, methyl or phenyl, with $R_1$ preferably being hydrogen, $C_1$–$C_{12}$ alkyl, allyl, benzyl, acetyl or acryloyl; and $R_2$ when n is 1 is hydrogen, $C_1$–$C_{18}$ alkyl optionally interrupted by one or more oxygen atoms, cyanoethyl, benzyl, glycidyl, a monovalent radical of an aliphatic, cycloaliphatic, araliphatic or aromatic carboxylic acid, or of carbamic acid or of a phosphorus-containing acid, or a monovalent silyl radical, preferably a radical of an aliphatic carboxylic acid having 2-18 C atoms, of a cycloaliphatic carboxylic acid having 5-12 C atoms or of an aromatic carboxylic acid having 7-15 C atoms; $R_2$ when n is 2 is $C_1$–$C_{12}$ alkylene, $C_4$–$C_{12}$ alkenylene, xylylene, a bivalent radical of an aliphatic, cycloaliphatic, araliphatic or aromatic dicarboxylic acid, of dicarbamic acid or of a phosphorus-containing acid, or a bivalent silyl radical, preferably a radical of an aliphatic dicarboxylic acid having 2-36 C atoms, of a cycloaliphatic or aromatic dicarboxylic acid having 8-14 C atoms, or of an aliphatic, cycloaliphatic or aromatic dicarbamic acid having 8-14 C atoms; $R_2$ when n is 3 is a trivalent radical of an aliphatic, cycloaliphatic or aromatic tricarboxylic acid, of an aromatic tricarbamic acid or of a phosphorus-containing acid, or a trivalent silyl radical; and $R_2$ when n is 4 is a tetravalent radical of an aliphatic, cycloaliphatic or aromatic tetracarboxylic acid.

If any substituents are $C_1$–$C_{12}$ alkyl, they are for example methyl, ethyl, n-propyl, n-butyl, sec-butyl, tert-butyl, n-hexyl, n-octyl, 2-ethyl-hexyl, n-nonyl, n-decyl, n-undecyl or n-dodecyl.

As $C_1$–$C_{18}$ alkyl, $R_1$ or $R_2$ can be for example the groups given above, and in addition for example n-tridecyl, n-tetradecyl, n-hexadecyl or n-octadecyl.

When $R_1$ is $C_3$–$C_8$ alkenyl, it can be for example 1-propenyl, allyl, methallyl, 2-butenyl, 2-pentenyl, 2-hexenyl, 2-octenyl or 4-tert-butyl-2-butenyl.

As $C_3$–$C_8$ alkynyl, $R_1$ is preferably propargyl.

$R_1$ as $C_7$–$C_{12}$ aralkyl is in particular phenethyl or especially benzyl.

As $C_1$–$C_8$ alkanoyl, $R_1$ is for example formyl, propionyl, butyryl, octanoyl but preferably acetyl, and as $C_3$–$C_5$ alkenoyl, $R_1$ is particularly acryloyl.

If $R_2$ is a monovalent radical of a carboxylic acid, it is for example a radical of acetic acid, stearic acid, salicylic acid, methacrylic acid, maleic acid, benzoic acid or β-(3,5-di-tert-butyl-4-hydroxyphenyl)-propionic acid.

If $R_2$ is a bivalent radical of a dicarboxylic acid, it is for example a radical of adipic acid, suberic acid, sebacic acid, maleic acid, phthalic acid, bibutylmalonic acid, dibenzylmalonic acid or butyl-(3,5-di-tert-butyl-4-hydroxybenzyl)-malonic acid, or bicycloheptenedicarboxylic acid.

If $R_2$ is a triavalent radical of a tricarboxylic acid, it is for example a radical of trimellitic acid or of nitrilotriacetic acid.

If $R_2$ is a tetravalent radical of a tetracarboxylic acid, it is for example a radical of pyromellitic acid or butane-1,2,3,4-tetracarboxylic acid.

If $R_2$ is a bivalent radical of a dicarbamic acid, it is for example a radical of hexamethylenedicarbamic acid or of 2,4-toluylenedicarbamic acid.

The following compounds are examples of polyalkylpiperidine light stabilizers of this class:

(1) 4-hydroxy-2,2,6,6-tetramethylpiperidine,
(2) 1-allyl-4-hydroxy-2,2,6,6-tetramethylpiperidine,
(3) 1-benzyl-4-hydroxy-2,2,6,6-tetramethylpiperidine,
(4) 1-(4-tert-butyl-2-butenyl)-4-hydroxy-2,2,6,6-tetramethylpiperidine,
(5) 4-stearoyloxy-2,2,6,6-tetramethylpiperidine,
(6) 1-ethyl-4-salicyloyloxy-2,2,6,6-tetramethylpiperidine,
(7) 4-methacryloyloxy-1,2,2,6,6-pentamethylpiperidine,
(8) 1,2,2,6,6-pentamethylpiperidin-4-yl-β-(3,5-ditert-butyl-4-hydroxyphenyl)-propionate,
(9) 1-benzyl-2,2,6,6-tetramethyl-4-piperidinylmaleinate,
(10) (di-2,2,6,6-tetramethylpiperidin-4-yl)-adipate
(11) (di-2,2,6,6-tetramethylpiperidin-4-yl)-sebacate,
(12) (di-1,2,3,3,6-trimethyl-2,6-diethyl-piperidin-4-yl)sebacate,
(13) (di-1-allyl-2,2,6,6-tetramethyl-piperidin-4-yl)phthalate,
(14) 1-propargyl-4-β-cyanoethyloxy-2,2,6,6-tetramethylpiperidine,

(15) 1-acetyl-2,2,6,6-tetramethylpiperidin-4-yl-acetate,
(16) trimellitic acid-tri-(2,2,6,6-tetramethylpiperidin-4-yl)ester,
(17) 1-acryloyl-4-benzyloxy-2,2,6,6-tetramethyl-piperidine,
(18) dibutyl-malonic acid-di-(1,2,2,6,6-pentamethyl-piperidin-4-yl)ester,
(19) butyl-(3,5-di-tert-butyl-4-hydroxybenzyl)-malonic acid-di-(1,2,2,6,6-pentamethylpiperidin-4-yl)ester,
(20) dibenzyl-malonic acid-di-(1,2,2,6,6-pentamethyl-piperidin-4-yl)ester,
(21) dibenzyl-malonic acid-di-(1,2,3,6-tetramethyl-2,6-diethyl-piperidin-4-yl)ester,
(22) hexane-1',6'-bis-(4-carbamoyloxy-1-n-butyl-2,2,6,6-tetramethylpiperidine),
(23) toluene-2',4'-bis-(4-carbamoyloxy-1-n-propyl-2,2,6,6-tetramethylpiperidine),
(24) dimethyl-bis-(2,2,6,6-tetramethylpiperidine-4-oxy)silane,
(25) phenyl-tris-(2,2,6,6-tetramethylpiperidine-4-oxy)silane,
(26) tris-(1-propyl-2,2,6,6-tetramethylpiperidin-4-yl)phosphite,
(27) tris-(1-propyl-2,2,6,6-tetramethylpiperidin-4-yl)phosphate, and
(28) phenyl-[bis-(1,2,2,6,6-pentamethylpiperidin-4-yl)]phosphonate
(29) di(1,2,2,6,6-pentamethylpiperidin-4-yl)sebacate
(b) Light stabilisers of the formula (III)

$$\left[ \begin{array}{c} RCH_2 \quad CH_3 \; R \\ R_1-N \quad \overset{R_3}{\underset{|}{N}}-R_4 \\ RCH_2 \quad CH_3 \end{array} \right]_n \quad (III)$$

in which n is the number 1 or 2; R is as defined under the formula I; $R_1$ is as defined under (a); $R_3$ is hydrogen, $C_1$–$C_{12}$ alkyl, $C_5$–$C_7$ cycloalkyl, $C_7$–$C_8$ aralkyl, $C_2$–$C_{18}$ alkanoyl, $C_3$–$C_5$ alkenoyl or benzoyl; and $R_4$, when n is 1, is hydrogen, $C_1$–$C_{18}$ alkyl, $C_3$–$C_8$ alkenyl, $C_5$–$C_7$ cycloalkyl, $C_2$–$C_8$ alkyl substituted by a cyano, carbonyl or carbamide group, or it is glycidyl, a group of the formula —CH$_2$—CH(OH)—Z or of the formula —CONH—Z wherein Z is hydrogen, methyl or phenyl; or $R_4$ when n is 2 is $C_2$–$C_{12}$ alkylene, $C_6$–$C_{12}$ arylene, xylylene, a —CH$_2$—CH(OH)—CH$_2$ group, or a group —CH$_2$—CH(OH)—CH$_2$—O—X—O—CH$_2$—CH(OH)—CH$_2$— wherein X is $C_2$–$C_{10}$ alkylene, $C_6$–$C_{15}$ arylene or $C_6$–$C_{12}$ cycloalkylene; or, provided that $R_3$ is not alkanoyl, alkenoyl or benzoyl, $R_4$ can also be a bivalent radical of an aliphatic, cycloaliphatic or aromatic dicarboxylic acid or dicarbamic acid, or can be the group —CO—; or $R_3$ and $R_4$ together when n is 1 can be the cyclic radical of an aliphatic or aromatic 1,2- or 1,3-dicarboxylic acid.

If any substituents are $C_1$–$C_{18}$ alkyl, they are as already defined under (a).

If any substituents are $C_5$–$C_7$ cycloalkyl, they are in particular cyclohexane.

As $C_7$–$C_8$ aralkyl, $R_3$ is particularly phenethyl or above all benzyl.

As $C_2$–$C_{18}$ alkanoyl, $R_3$ is for example propionyl, butyryl, octanoyl, dodecanoyl, hexadecanoyl, octadecanoyl but preferably acetyl; and as $C_3$–$C_5$ alkenoyl, $R_3$ is in particular acryloyl.

If $R_4$ is $C_2$–$C_8$ alkenyl unsubstituted or substituted by a cyano, carbonyl or carbamide group, it is for example 1-propenyl, allyl, methallyl, 2-butenyl, 2-pentenyl, 2-hexenyl, 2-octenyl, 2,2-dicyanovinyl, 1-methyl-2-cyano-2-methoxycarbonyl-vinyl or 2,2-diacetylaminovinyl.

If any substituents are $C_2$–$C_{12}$ alkylene, they are for example ethylene, propylene, 2,2-dimethylpropylene, tetramethylene, hexamethylene, octamethylene, decamethylene or dodecamethylene.

If any substituents are $C_6$–$C_{15}$ arylene, they are for example o-, m- or p-phenylene, 1,4-naphthylene or 4,4'-diphenylene.

As $C_6$–$C_{12}$ cycloalkylene, X is especially cyclohexylene.

The following compounds are examples of polyalkylpiperidine light stabilisers of this class:

(30) N,N'-bis-(2,2,6,6-tetramethylpiperidin-4-yl)hexamethylene-1,6-diamine,
(31) N,N'-bis-(2,2,6,6-tetramethylpiperidin-4-yl)hexamethylene-1,6-diacetamide,
(32) 1-acetyl-4-(N-cyclohexylacetamido)-2,2,6,6-tetramethylpiperidine,
(33) 4-benzylamino-2,2,6,6-tetramethylpiperidine,
(34) N,N'-bis-(2,2,6,6-tetramethylpiperidin-4-yl)-N,N'-dibutyladipamide,
(35) N,N'-bis-(2,2,6,6-tetramethylpiperidin-4-yl)-N,N'-dicyclohexyl-(2-hydroxypropylene),
(36) N,N'-bis-(2,2,6,6-tetramethylpiperidin-4-yl)-p-xylylenediamine,
(37) the compound of the formula

[structure showing two 1-methyl-2,2,6,6-tetramethylpiperidine units connected via —N(C$_4$H$_9$)—CH$_2$—CH(CH)—CH$_2$—O— linkages to a bisphenol-type central unit with CH$_3$—O—CH$_3$]

(38) 4-(bis-2-hydroxyethyl)-amino-1,2,2,6,6-pentamethylpiperidine,
(39) 4-(3-methyl-4-hydroxy-5-tert-butyl-benzoic acidamido)-2,2,6,6-tetramethylpiperidine, and
(40) 4-methacrylamino-1,2,2,6,6-pentamethylpiperidine.

(c) Light stabilisers of the formula (IV)

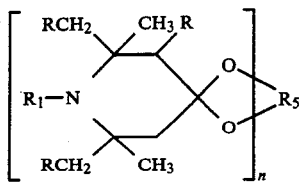

in which n is the number 1 or 2; R is as defined under the formula (I); R₁ is as defined under (a); and R₅, when n is 1 is C₂-C₈ alkylene or hydroxyalkylene or C₄-C₂₂ acyloxyalkylene; and R₅, when n is 2, is the group (—CH₂)₁₂C(CH₂—)₂.

If R₅ is C₂-C₈ alkylene or hydroxyalkylene, it is for example ethylene, 1-methyl-ethylene, propylene, 2-ethylpropylene or 2-ethyl-2-hydroxymethylpropylene.

As C₄-C₂₂ acyloxyalkylene, R₅ is for example 2-ethyl-2-acetoxymethyl-propylene.

The following compounds are examples of polyalkylpiperidine light stabilisers of this class:

(41) 9-aza-8,8,10,10-tetramthyl-1,5-dioxaspiro[5.5]undecane,

(42) 9-aza-8,8,10,10-tetramethyl-3-ethyl-1,5-dioxaspiro[5.5]undecane,

(43) 8-aza-2,7,7,8,9,9-hexamethyl-1,4-dioxaspiro[4.5]decane,

(44) 9-aza-3-hydroxymethyl-3-ethyl-8,8,9,10,10-pentamethyl-1-5-dioxaspiro[5.5]undecane.

(45) 9-aza-3-ethyl-3-acetoxymethyl-9-acetyl-8,8,10,10-tetramethyl-1,5-dioxaspiro[5.5]undecane, and

(46) 2,2,6,6-tetramethylpiperidine-4-spiro-2′-(1′,3′-dioxane)5′-spiro-5″-(1″,3″-dioxane)-2″-spiro-4‴-(2‴,2‴,6‴,6‴-tetramethylpiperidine).

(d) Light stabilisers of the formulae (VA), (VB), and (VC)

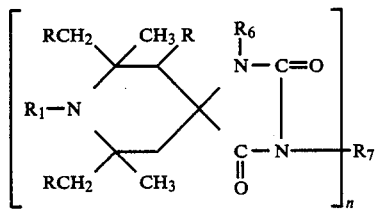

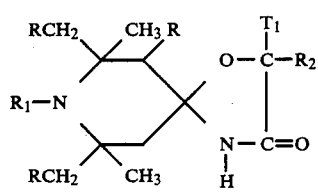

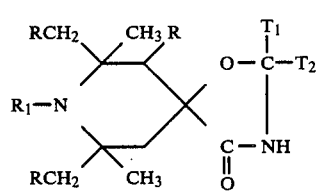

in which n is the number 1 or 2; R is as defined under the formula (I); R₁ is as defined under (a); R₆ is hydrogen, C₁-C₁₂ alkyl allyl benzyl glycidyl or C₂-C₆alkoxyalkyl and R₇ when n is 1; is hydrogen, C₁-C₁₂ alkyl, C₃-C₅ alkenyl, C₇-C₉ aralkyl, C₅-C₇ cycloalkyl C₂-C₄ hydroxylakyl, C₂-C₆ alkoxyalyl C₆-C₁₀ aryl, glycidyl, a group of the formula —(CH)—COO—Q or of the formula —(CH₂)ₘ—O—CO—Q wherein m is 1 or 2, and Q is C₁-C₄ alkyl or phenyl; or R₇, when n is 2, is C₂-C₁₂ alkylene, C₆-C₁₂ arylene, a group —CH₂—CH(OH)—CH₂—O—X—O—CH₂—CH(OH)—CH₂— wherein X is C₂-C₁₀ alkylene, C₆-C₁₅ arylene or C₆-C₁₂ cycloalkylene, or a group —CH₂CH(OZ′)CH₂—(OCH₂—CH(OZ′)CH₂)₂— wherein Z′ is hydrogen, C₁-C₁₈ alkyl, allyl, benzyl, C₂-C₁₂ alkanoyl or benzoyl, and T₁ and T₂ independently of another are hydrogen, C₁-C₁₈ alkyl or C₆-C₁₀ aryl which is unsubstituted or substituted by halogen or C₁-C₄ alkyl, or C₁-C₉ aralkyl, or T₁ and T₂ together with the C atom which bonds them form C₅-C₇ cycloalkyl, pyrrolidinyl or piperidinyl, which are unsubstituted or substituted by C₁-C₄ alkyl.

If any substituents are C₁-C₁₂ alkyl, they are for example methyl, ethyl, n-propyl, n-butyl, sec-butyl, tert-butyl, n-hexyl, n-octyl, 2-ethyl-hexyl, n-nonyl, n-decyl, n-undecyl or n-dodecyl.

As for C₁-C₁₈ alkyl, they can be for example the groups stated above, and in addition for example n-tridecyl, n-tetradecyl, n-hexadecyl or n-octadecyl.

If any substituents are C₂-C₆ alkoxyalkyl, they are for example methoxymethyl, ethoxymethyl, propoxymethyl, tert-butoxymethyl, ethoxyethyl, ethoxypropyl, n-butoxyethyl, tert-butoxyethyl, isopropoxyethyl or propoxypropyl.

If any group is C₃-C₅ alkenyl, it is for example 1-propenyl, allyl, methallyl, 2-butenyl or 2-pentenyl.

As for C₇-C₉ aralkyl, they are in particular phenethyl or above all benzyl and as C₅-C₇ cycloalkyl, or T₁+T₂+ the C atom, R₇ is especially cyclohexyl.

If R₇ is C₂-C₄ hydroxyalkyl, it is for example 2-hydroxyethyl, 2-hydroxypropyl, 3-hydroxypropyl, 2-hydroxybutyl or 4-hydroxybutyl.

As for C₆-C₁₀ aryl, they are in particular phenyl, or α- or β-naphthyl which is unsubstituted for substituted by halogen or C₁-C₄ alkyl.

If R₇ is C₂-C₁₂ alkylene, it is for example ethylene, propylene, 2,2-dimethylpropylene, tetramethylene, hexamethylene, octamethylene, decamethylene or dodecamethylene.

If R₇ is C₆-C₁₂ arylene, it is for example o-, m- or p-phenylene, 1,4-naphthylene or 4,4′-diphenylene.

If Z′ is C₂-C₁₂ alkanoyl, it is for example propionyl, butyryl, octanoyl, dodecanoyl or preferably acetyl.

As C₂-C₁₀ alkylene, C₆-C₁₅ arylene or C₆-C₁₂ cycloalkylene, X has the meaning given under (b).

The following compounds are examples of polyalkylpiperidine light stabilisers of this class:

(47) 3-benzyl-1,3,8-triaza-7,7,9,9-tetramethylspiro[4.5]decane-2,4-dione,

(48) 3-n-octyl-1,3,8-triaza-7,7,9,9-tetramethylspiro[4.5]decane-2,4-dione,

(49) 3-allyl-1,3,8-triaza-1,7,7,9,9-pentamethylspiro[4.5]decane-2,4-dione,

(50) 3-glycidyl-1,3,8-triaza-7,7,8,9,9-pentamethylspiro[4.5]decane-2,4-dione, (50a) 2-isopropyl-7,7,9,9-tetramethyl-1-oxa-3,8-diaza-4-oxyspiro[4.5]decane (50b) 2-butyl-7,7,9,9-tetramethyl-1-oxa-3,8-diaza-4-oxyspiro[4.5]decane (50c) 2-isopropyl-7,7,9,9-tetramethyl-1-oxa-4,8-diaza-3-oxyspiro[4.5]decane, (50d) 2-butyl-7,7,9,9-tetramethyl-1-oxa-4,8-diaza-3-oxyspiro[4.5]decane.

or the compounds of the following formulae:

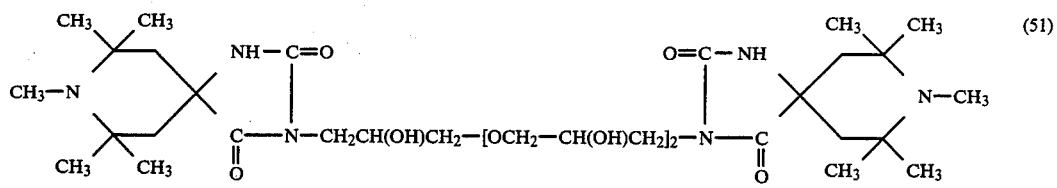
(51)

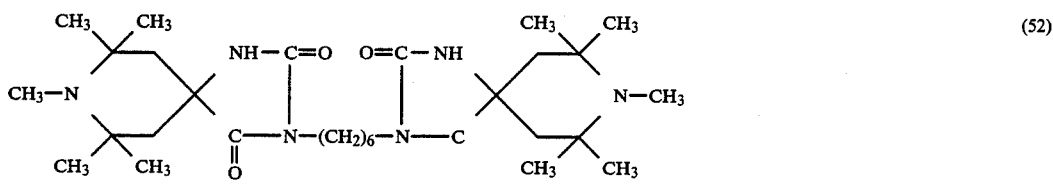
(52)

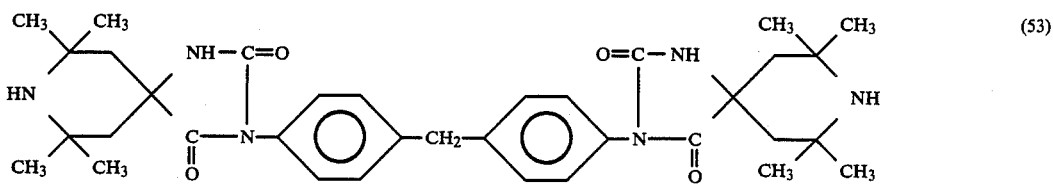
(53)

(e) Light stabilisers of the formula (VI)

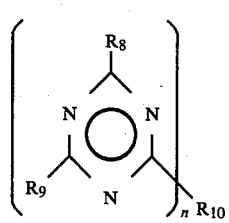
(VI)

in which n is the number 1 or 2, and $R_8$ is a group of the formula

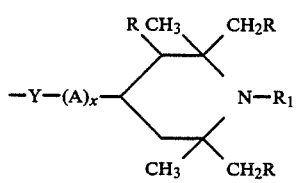

in which R is as defined under the formula (I), $R_1$ is as defined under (a), Y is —O— or —NR$_{11}$—, A is $C_2$–$C_6$ alkylene; and X is the number 0 or 1; $R_9$ is the groups $R_8$, NR$_{11}$R$_{12}$, —OR$_{13}$, —NHCH$_2$OR$_{13}$ or —N(CH$_2$OR$_{13}$)$_2$; $R_{10}$ when n is 1 is the groups $R_8$ or $R_9$, and $R_{10}$ when n is 2 is the group —Y—β—Y— wherein β is $C_2$–$C_6$ alkylene optionally interrupted by —N(R$_{11}$)—; $R_{11}$ is $C_1$–$C_{12}$ alkyl, cyclohexyl, benzyl or $C_1$–$C_4$ hydroxyalkyl, or a group of the formula

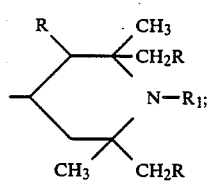

$R_{12}$ is $C_1$–$C_{12}$ alkyl, cyclohexyl, benzyl or $C_1$–$C_4$ hydroxyalkyl; $R_{13}$ is hydrogen, $C_1$–$C_{12}$ alkyl or phenyl; or $R_{11}$ and $R_{12}$ together are $C_4$–$C_5$ alkylene or oxaalkylene, or $R_{11}$ and $R_{12}$ are each a group of the formula

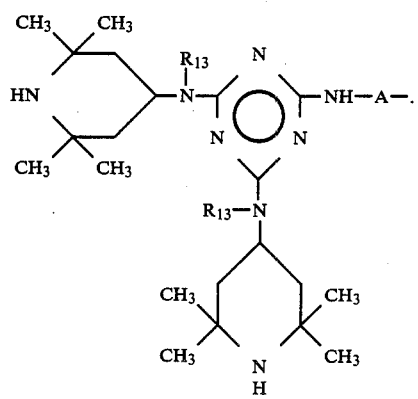

If any substituents are $C_1$–$C_{12}$ alkyl, they are for example methyl, ethyl, n-propyl, n-butyl, sec-butyl, tert-butyl, n-hexyl, n-octyl, 2-ethylhexyl, n-nonyl, n-decyl, n-undecyl or n-dodecyl.

If any substituents are $C_1$–$C_4$ hydroxyalkyl, they are for example 2-hydroxyethyl, 2-hydroxypropyl, 3-hydroxypropyl, 2-hydroxybutyl or 4-hydroxybutyl.

If A is $C_2$–$C_6$ alkylene, it is for example ethylene, propylene, 2,2-dimethylpropylene, tetramethylene or hexamethylene.

If $R_{11}$ and $R_{12}$ together are $C_4$–$C_5$ alkylene or oxaalkylene, this is for example tetramethylene, pentamethylene or 3-oxapentamethylene.

The compounds of the following formulae are examples of polyalkylpiperidine light stabilisers of this class:

(54)
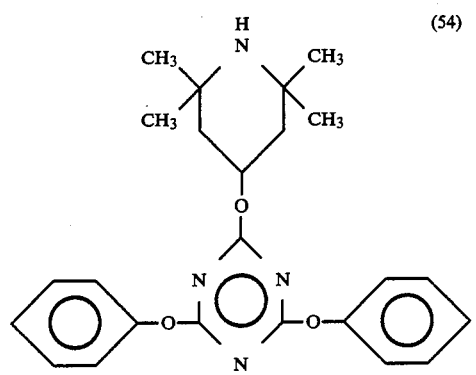
(55)
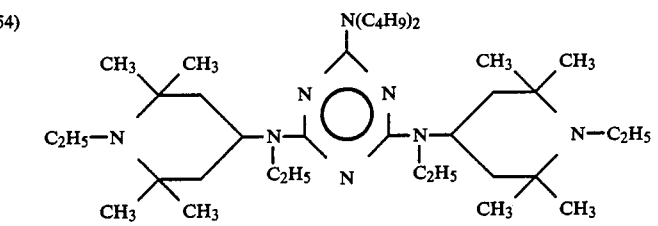
(56)
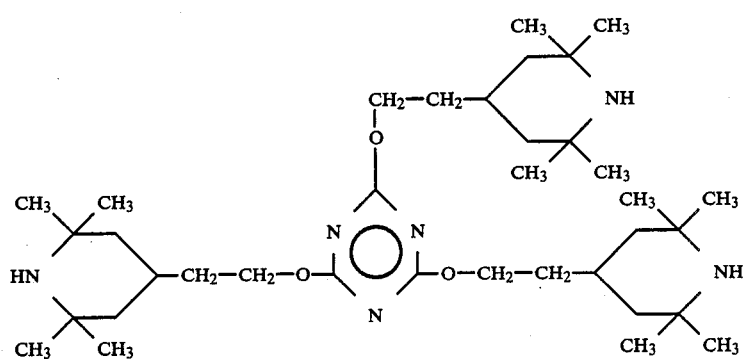
(57)
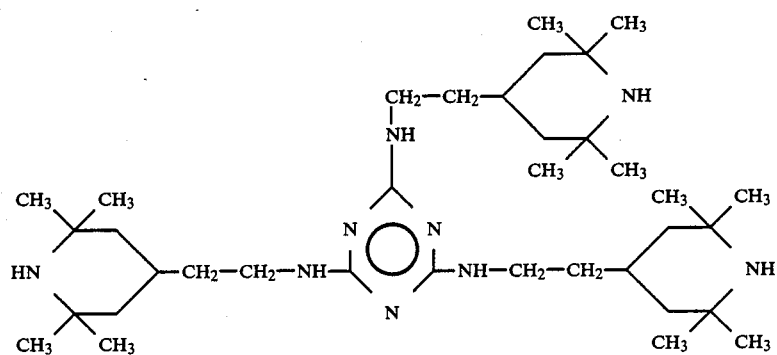
(58)
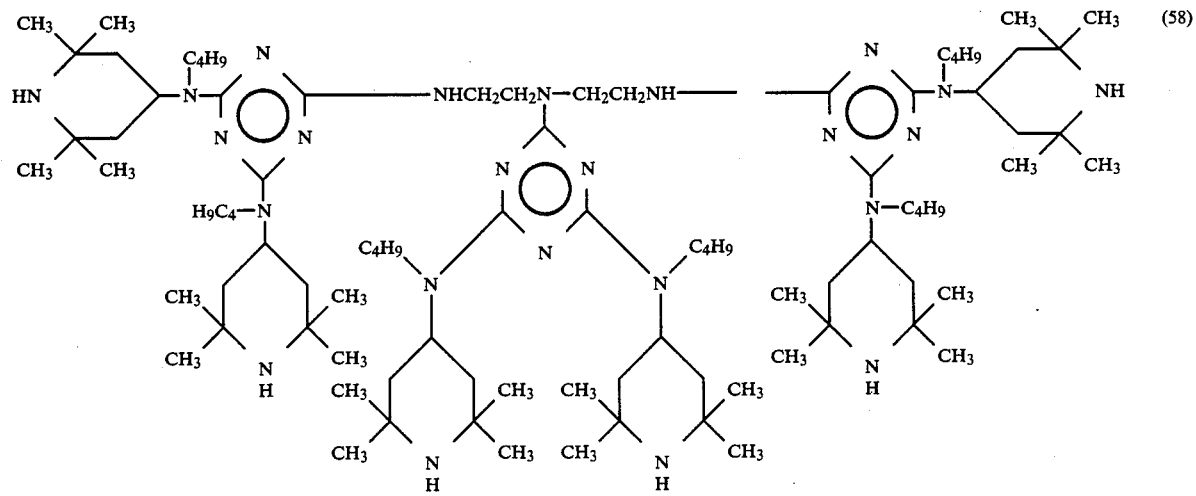

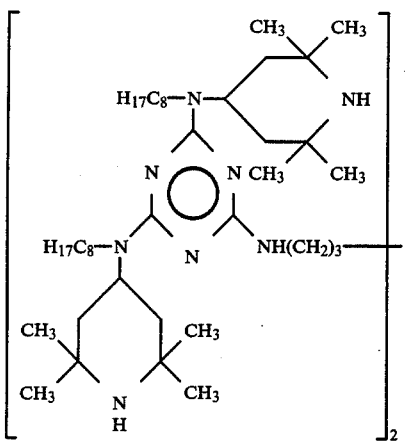

(59)

(f) Light stabilisers of the formula (VII)

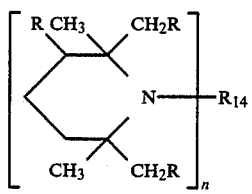

(VII)

in which n is the number 1 or 2; R is as defined under the formula (I); and $R_{14}$ when n is 1 is $C_4$-$C_{18}$ alkyl, $C_7$-$C_{12}$ aralkyl, the group —CO—$R_{15}$, or $C_1$-$C_4$ alkyl which is substituted by —CN, —COO$R_{16}$, —OH, —OCO$R_{17}$ or

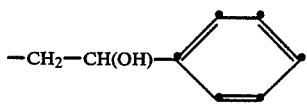

wherein $R_{15}$ is $C_1$-$C_{12}$ alkyl, $C_2$-$C_4$ alkenyl or phenyl, $R_{16}$ is $C_1$-$C_{18}$ alkyl, $R_{17}$ is $C_1$-$C_{18}$ alkyl, $C_2$-$C_{10}$ alkenyl, cyclohexyl, benzyl or $C_6$-$C_{10}$ aryl; or $R_{14}$ when n is 2 is $C_4$-$C_{12}$ alkylene, 2-butenylene-1,4,xylylene, the group —(CH$_2$)$_2$—OOC—$R_{18}$—COO—(OH$_2$)$_2$— or the group —CH$_2$—OOC—$R_{19}$—COO—CH$_2$— wherein $R_{18}$ is $C_2$-$C_{10}$ alkylene, phenylene or cyclohexylene, and $R_{19}$ is $C_2$-$C_{10}$ alkylene, xylylene or cyclohexylene.

If any substituents are $C_1$-$C_{12}$ alkyl, they are for example methyl, ethyl, n-propyl, n-butyl, sec-butyl, tert-butyl, n-hexyl, n-octyl, 2-ethyl-hexyl, n-nonyl, n-decyl, n-undecyl or n-dodecyl.

Any substituents which are $C_1$-$C_{18}$ alkyl can be for example the groups mentioned above, and in addition for example n-tridecyl, n-tetradecyl, n-hexadecyl or n-octadecyl.

If any groups are $C_2$-$C_{10}$ alkylene, these are in particular ethylene, propylene, 2,2-dimethylpropylene, tetramethylene, hexamethylene, octamethylene or decamethylene.

As $C_4$-$C_{18}$ alkyl, $R_{14}$ is for example n-butyl, sec-butyl, tert-butyl, n-hexyl, n-octyl, 2-ethyl-hexyl, 1,1-dimethyl-2-tert-butylethyl, n-nonyl, n-decyl, n-dodecyl, n-tridecyl, n-tetradecyl, n-hexadecyl or n-octadecyl.

If $R_{14}$ is a $C_1$-$C_4$ alkyl group substituted by —CN, it is for example cyanomethyl, cyanoethyl, 3-cyano-n-propyl or 4-cyano-n-butyl.

If $R_{14}$ is $C_4$-$C_{12}$ alkylene, it is for example 2,2-dimethylpropylene, tetramethylene, hexamethylene, octamethylene, decamethylene or dodecamethylene.

If $R_{14}$ is $C_7$-$C_{12}$ aralkyl, it is in particular phenethyl, p-methyl-benzyl or especially benzyl.

As $C_2$-$C_4$ alkenyl, $R_{15}$ is for example vinyl, 1-propenyl, allyl, methallyl or 2-butenyl.

As $C_2$-$C_{10}$ alkenyl, $R_{17}$ is for example the groups mentioned for $R_{15}$ as alkenyl, and in addition for example crotyl, 2-hexenyl, 2-octenyl or 2-decenyl.

If $R_{17}$ is $C_6$-$C_{10}$ aryl, it is for example phenyl which is unsubstituted or substituted in the o- or p-position by methyl, ethyl, isopropyl, n-butyl or tert-butyl.

The following compounds are examples of polyalkylpiperidine light stabilisers of this class:

(60) bis-[β-(2,2,6,6-tetramethylpiperidino)-ethyl]-sebacate,

(61) α-(2,2,6,6-tetramethylpiperidino)-acetic acid-p-octyl ester, and

(62) 1,4-bis-(2,2,6,6-tetramethylpiperidino)-2-butene.

(g) Light stabilisers of the formula (VIII)

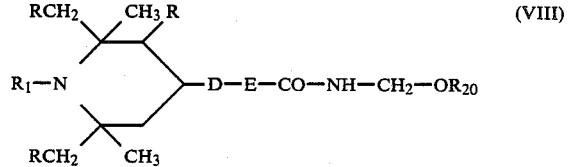

(VIII)

in which D is —N($R_{21}$)— or —O—; E is $C_1$-$C_3$ alkylene, the group —CH$_2$—CH(Z)—O— wherein Z is hydrogen, methyl or phenyl, the group —(CH$_2$)$_3$—NH— or a single bond; R is hydrogen or methyl; $R_1$ is hydrogen, $C_1$-$C_{18}$ alkyl, $C_3$-$C_8$ alkenyl, $C_3$-$C_8$ alkynyl, $C_7$-$C_{12}$ aralkyl, $C_1$-$C_8$ alkanoyl, $C_3$-$CA_5$ alkenoyl or glycidyl; $R_{20}$ is hydrogen or $C_1$-$C_{18}$ alkyl; $R_{31}$ is hydrogen, $C_1$-$C_{18}$ alkyl, $C_5$-$C_7$ cycloalkyl, $C_7$-$C_{12}$ aralkyl, cyanoethyl, $C_6$-$C_{10}$ aryl, the group —CH$_2$—CH(Z)—OH wherein Z has the meaning defined above, a group of the formula

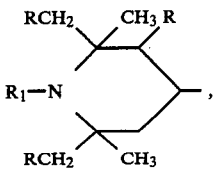

or a group of the formula

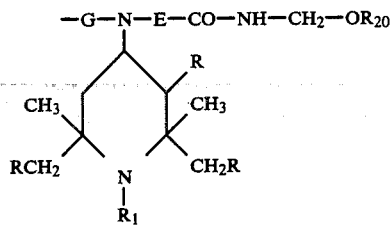

wherein G can be $C_2$–$C_6$ alkylene or $C_6$–$C_{12}$ arylene; or $R_{21}$ is a group —E—CO—NH—$CH_2$—$OR_{20}$.

If any substituents are $C_1$–$C_{18}$ alkyl, they are for example methyl, ethyl, n-propyl, n-butyl, sec-butyl, tert-butyl, n-hexyl, n-octyl, 2-ethyl-hexyl, n-nonyl, n-decyl, n-undecyl, n-dodecyl, n-tridecyl, n-tetradecyl, n-hexadecyl or n-octadecyl.

If any substituents are $C_7$–$C_{12}$ aralkyl, they are for example phenethyl or in particular benzyl.

If $R_1$ is $C_3$–$C_8$ alkenyl, it can be for example 1-propenyl, allyl, methallyl, 2-butenyl, 2-pentenyl, 2-hexenyl, 2-octenyl or 4-tert-butyl-2-butenyl.

As $C_3$–$C_8$ alkynyl, $R_1$ is preferably propargyl. As $C_1$–$C_8$ alkanoyl, $R_1$ is for example formyl, propionyl, butyryl, octanoyl but preferably acetyl; and as $C_3$–$C_5$ alkenoyl, $R_1$ is especially acryloyl.

As $C_5$–$C_7$ cycloalkyl, $R_{21}$ is in particular cyclohexyl.

As $C_6$–$C_{10}$ aryl, $R_{21}$ is particularly phenyl, or α- or β-naphthyl which is unsubstituted or substituted with halogen or $C_1$–$C_4$ alkyl. As $C_1$–$C_3$ alkylene, E is for example methylene, ethylene or propylene.

As $C_2$–$C_6$ alkylene, G is for example ethylene, propylene, 2,2-dimethylpropylene, tetramethylene or hexamethylene; and as $C_6$–$C_{12}$ arylene, G is o-, m- or p-phenylene, 1,4-naphthylene or 4,4'-diphenylene.

The following compounds are examples of polyalkylpipierdine light stabilisers of this class:

(63) N-hydroxymethyl-N'-2,2,6,6-tetramethylpiperidin-4-yl-urea,

(64) N-methoxymethyl-N'-2,2,6,6-tetramethylpiperidin-4-yl-urea,

(65) N-methoxymethyl-N'-n-dodecyl-N'-2,2,6,6-tetramethylpiperidin-4-yl-urea, and

(66) O-(2,2,6,6-tetramethylpiperidin-4-yl)-N-methoxymethyl-urethane.

(h) Polymeric compounds of which the recurring structural unit contains a polyalkylpiperidine radical of the formula (I), especially polyesters, polyethers, polyamides, polyamines, polyurethanes, polyureas, polyaminotriazines, poly(meth)acrylates or poly(meth)acrylamides, and copolymers thereof which contain such radicals.

The compounds of the following formulae, wherein m is a number from 2 to about 200 inclusive, are examples of polyalkylpiperidine light stabilisers of this class.

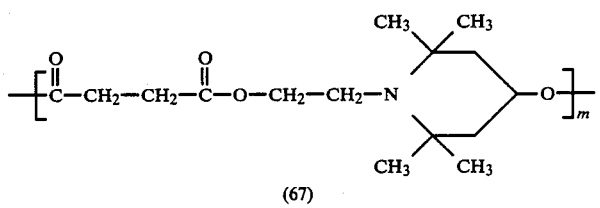

(67)

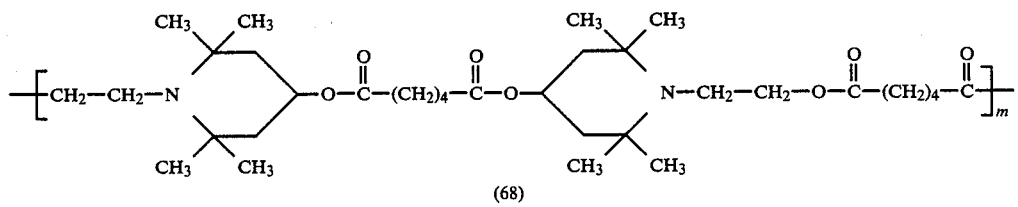

(68)

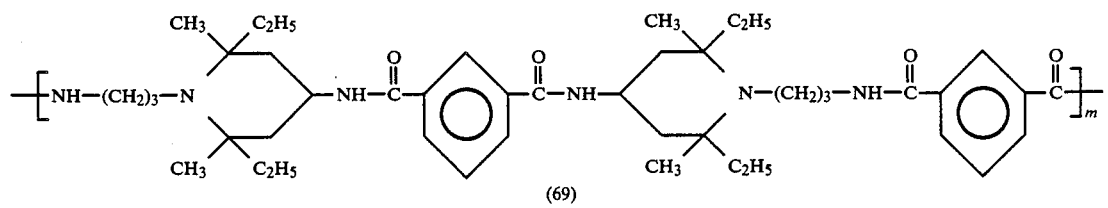

(69)

-continued

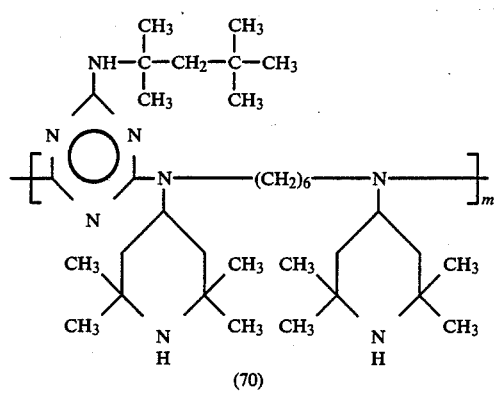
(70)

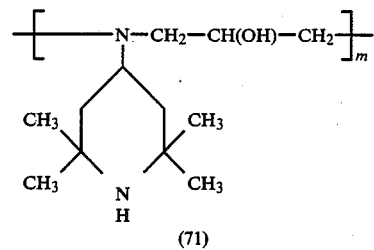
(71)

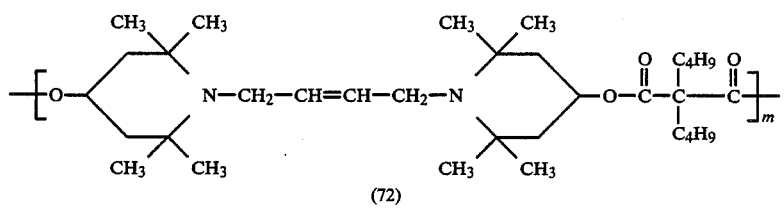
(72)

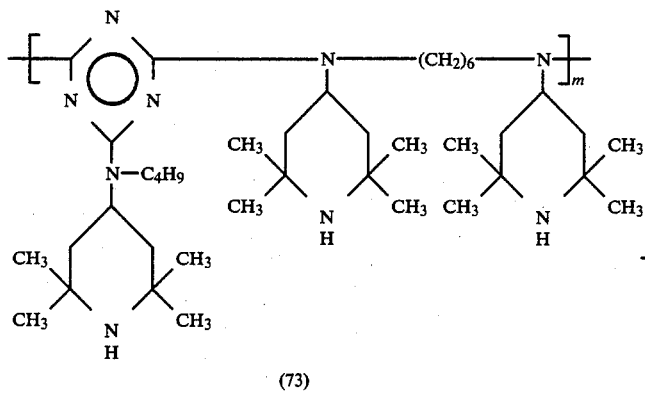
(73)

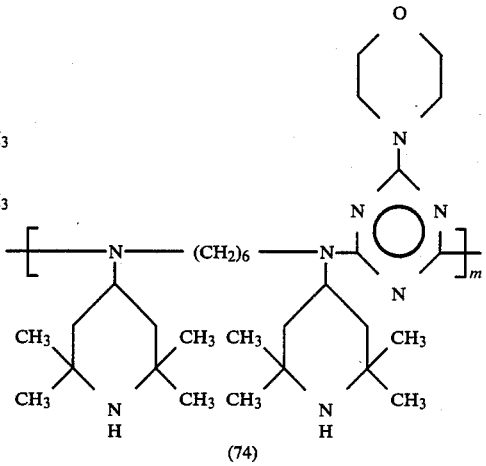
(74)

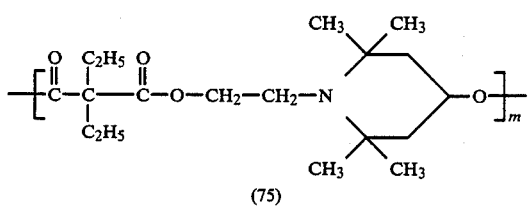
(75)

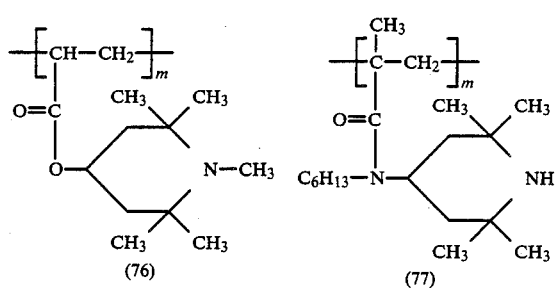
(76) (77)

(i) Light stabilizers of the formula IX

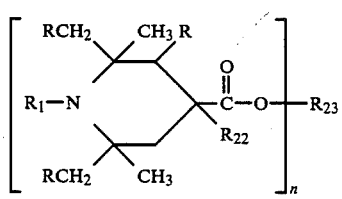 (IX)

in which n is a number from 1-4 inclusive, preferably 1 or 2; R is as defined under the formula (I); $R_1$ is hydrogen, oxyl, $C_1$-$C_{18}$ alkyl, $C_3$-$C_8$ alkenyl, $C_3$-$C_8$ alkynyl, $C_7$-$C_{12}$ aralkyl, $C_1$-$C_8$ alkanoyl, $C_3$-$C_5$ alkenoyl, glycidyl, a group —$CH_2CH(OH)$—Z wherein Z is hydrogen, methyl or phenyl, with $R_1$ preferably being hydrogen, $C_1$-$C_{12}$ alkyl, allyl, benzyl, acetyl or acryloxyl; $R_{22}$ is hydrogen, hydroxyl or $C_1$-$C_8$ alkoxy; and $R_{23}$, when n is 1, is $C_1$-$C_{20}$ alkyl $C_5$-$C_{12}$ cycloalkyl, $C_7$-$C_{14}$ aralkyl; when n is 2, $R_{23}$ is $C_2$-$C_{12}$ alkylene, $C_2$-$C_{12}$ cycloalkylene, $C_8$-$C_{16}$ cycloalkylene-dialkylene, $C_8$-$C_{14}$ aralkylene, $C_4$-$C_9$ mono- or dioxaalkylene; when n is 3, $R_{23}$ is $C_3$-$C_{12}$ alkane-triyl; and when n is 4, $R_{23}$ is $C_4$-$C_{12}$ alkane-tetrayl.

(j) Light stabilizers of the formula (X)

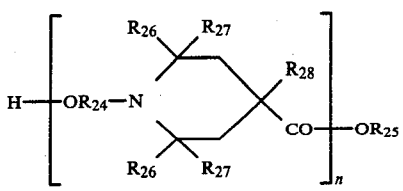

in which n is a number from 4–10 inclusive; $R_{24}$ is $C_2$–$C_8$ alkylene or $C_5$–$C_6$ cycloalkylene; $R_{25}$ is $C_1$–$C_8$ alkyl or $C_5$–$C_6$ cycloalkyl; $R_{26}$ and $R_{27}$ are $C_1$–$C_8$ alkyl or together form a $C_5$–$C_6$ cycloalkylene ring; and $R_{28}$ is hydrogen, hydroxyl, $C_1$–$C_8$ alkoxy or $C_1$–$C_8$ acyloxy.

Compounds having one of the following formulae are likewise applicable.

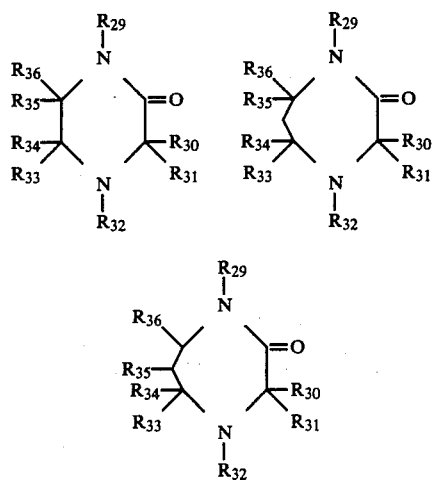

wherein $R_{29}$ and $R_{32}$ independently represent hydrogen, alkyl having from 1 to 24 carbon atoms, hydroxyalkyl having from 1 to 12 carbon atoms, haloalkyl having from 1 to 12 carbon atoms, cyanoalkyl having from 2 to 12 carbon atoms, aminoalkyl having from 1 to 12 carbon atoms, alkenyl having from 2 to 14 carbon atoms, and unsubstituted hydrocarbon aralkyl having from 7 to 14 carbon atoms;

$R_{32}$ optionally also represents oxygen, hydroxy or alkoxy;

$R_{30}$ and $R_{31}$ independently represent alkyl having from 1 to 12 carbon atoms, haloalkyl having from 1 to 12 carbon atoms, cyanoalkyl having from 2 to 12 carbon atoms, aminoalkyl having from 1 to 12 carbon atoms, cycloalkyl having from 5 to 14 carbon atoms, hydroxycycloalkyl having from 5 to 14 carbon atoms, alkenyl having from 2 to 14 carbon atoms, and unsubstituted hydrocarbon aralkyl having from 7 to 14 carbon atoms;

$R_{33}$, $R_{34}$, $R_{35}$, $R_{36}$ independently represent alkyl having from 1 to 12 carbon atoms, haloalkyl having from 1 to 12 carbon atoms, cyanoalkyl having from 2 to 12 carbon atoms, aminoalkyl having from 1 to 12 carbon atoms, alkenyl having from 2 to 14 carbon atoms, and unsubstituted hydrocarbon aralkyl having from 7 to 14 carbon atoms;

so that when $R_{30}$, $R_{31}$ is cyclized having from 4 to 6 unsubstituted methylene groups, and $R_{33}$, $R_{34}$ is also cyclized having from 4 to 6 unsubstituted methylene groups, each cyclized substituent is different;

$R_{35}$, $R_{36}$ additionally also represent hydrogen; and $R_{35}$, $R_{36}$ may when taken together with the carbon atom to which they are attached, form a polymethylene ring having from 5 to 6 carbon atoms.

Provided the polyalkylpiperidine derivatives are basic compounds, they can form salts with acids. Suitable acids are for example inorganic acids or organic carboxylic, sulfonic, phosphonic or phosphinic acids, such as hydrochloric acid, boric acid, phosphoric acid, acetic acid, salicyclic acid, toluenesulfonic acid or benzenephosphonic acid.

Applicable U.V. absorbers are also well known to those skilled in the art. Included among such applicable agents are:

1.1. 2-(2'-Hydroxyphenyl)-benzotriazoles, e.g. the 5'-methyl-, 3',5'-di-tert.-butyl-, 5'-tert.butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-alpha-methylbenzyl-5'-methyl-, 3'-alpha-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl-, 3',5'-bis(alpha,alpha-dimethylbenzyl), 3',5'-bis(alpha,alpha-dimethyl benzyl)-5-chloro-, 3',5'-di-tert.-octylphenyl, 3',5'-di-tert.-octylphenyl-5-chloro- and 5-chloro-3',5'-di-tert.-amyl-derivatives.

1.2. 2,4-bis-(2'-Hydroxyphenyl)-6-alkyl-s-triazines, e.g. the 6-ethyl-, 6-heptadecyl- or 6-undecyl-derivative.

1.3. 2-Hydroxybenzophenones, e.g. the 4-hydroxy-, 4-methoxy-, 4-octoxy-, 4-decyloxy-, 4-dodecyloxy-, 4-benzylozy-, 2',4-4'-trihydroxy- or 2'-hydroxy-4,4'-dimethoxy-dervative.

1.4. 1,3-bis-(2'-Hydroxybenzoyl)-benzenes, e.g. 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'dodecyloxy-benzoyl)-benzene.

1.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.

1.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or butyl ester or N-(β-carbomethoxyvinyl)-2-methyl-indoline.

1.7. Oxalic acid diamides, e.g. 4,4'-di-octyloxy-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-5,4'-di-tert.-butyl-oxanilide, or mixtures of ortho- and para-methoxy- as well as of o- and p-ethoxy-disubstituted oxanilides.

The benzotriazole U.V. absorbers are preferred for use in the instant invention. Typical benzotriazoles are described, for example, in U.S. Pat. Nos. 3,004,896, 3,189,615, 3,320,194, 4,127,586 and 4,283,327.

The term "fungicides" as utilized herein is intended to cover compounds covering a broad range of fungicidal, mildewcidal, preservative and antifouling activities, which compounds are subject to light-induced deterioration. Of particular interest are mildewcides and fungicides. Typical fungicides include carbamates such as 3-iodo-2-propynyl-butylcarbamate, dimethyldithiocarbamate, 2-sec.butyl-phenyl-N-methyl-carbamate, benzimidazol carbamates, carbamyl-(1-naphthyl-N-methylcarbamate), dithio carbaminate, (2-isopropoxyphenyl)-N-methylcarbamate, 4-(dimethylamino)-m- tolyl methylcarbamate, 6-chloro-3,4-xylyl methylcarbamate, zinc dimethyldithio carbamate and 1-naphthyl methylcarbamate; arsenic compounds such as copper chrome arsenate; chlorinated phenols such as tetrachloroprophenol, pentachlorophenol, sodium pentachlorophenate; copper compounds such as copper naphthenate; other chlorinated compounds such as 1-chloronaphthalene, N-trichloromethyl-thiophthalimide, tetrachloroisophthalonitrile, tetrachloropyridine-4-methyl-sulfonate, 2,4-dichloro-6-(o-chloroanilino)-s-triazine, 2,3-dichloro-1,4-naphthoquinone, α,α-bis(p-chlorophenyl)-3-pyridine-methanol and pentachloronitrobenzene; organo mercury compounds such as phenyl mercuric oleate and di(phenylmercury)dodecenyl succinate; organo tin compounds such as tributyl tin oxide; zinc compounds such as zinc naphthenate; ketones such as 2-n-octyl-4-isothiazolin-3-one, and 3,3'-ethylene bis[-tetrahydro-4,6-dimethyl-2H-1,3,5-thiadiazine-2-thione]; sulfonyl compounds such as 1,2-bis(N-propylsulfonyl)ethane; and iodomethyl p-tolyl sultone azole compounds such as 2-(4-thiazolyl)benzimidazole and $(Zn)_2$ mercapto benzothiazole; and other fungicides well known to those skilled in the art. Reference in this regard may be made to Torgeson, *Fungicides,* Vol. II, Chemistry and Physiology, Acedemic Press, New York (1969).

In general, each of the stabilizers of this invention is employed in concentrations of from about 0.25:1–4.0:1 and preferably 0.5:1 to 1.5:1, these ratios being determined relative to the weight of the fungicide material. Where the combined system is utilized, the piperidine compound and UV absorber are utilized in relative concentrations of from 16:1 to 1:16, and preferably 3:1 to 1:3. Specific concentrations within these ranges will depend on the nature of the fungicide, on the degree of stabilization required and on the nature of the substrate. The stabilizers may be readily incorporated by any conventional techniques at any convenient stage prior to the application of the fungicide or fungicide-containing formulation.

The stabilized polymer compositions of the invention may optionally also contain from about 0.1 to about 5%, preferably from about 0.5 to about 3% by weight of various conventional additives, such as the following, particularly phenolic antioxidants or metal deactivators, or mixtures thereof:

1. Antioxidants 1.1 Simple 2,6-dialkylphenols such as, for example, 2,6-ditert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl)adipate.

1.3 Hydroxylated thiodiphenyl esters, such as for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)disulfide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol, 4,4'-methylene-bis-(2,6-di-tert.-butylphenol), 2,6-di(3-tert.-butyl-5-methyl-2-hydroxybenzyl)-4-methylphenol, 2,2'-methylene-bis-[4-methyl-6-(α-methylcyclohexyl)-phenol], 1,1-bis(3,5-dimethyl-2-hydroxyphenyl)-butane, 1,1-bis-(5-tert.-butyl-4-hydroxy-b 2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)pentane and ethylene glycol bis-[3,3-bis-(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl)dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl]2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert-butyl-4-hydroxybenzyl)-2,3,5,6-tetramethylbenzene and 2,4,6-tri-(3,5-di-tert.-butyl-4-hydroxybenzyl)-phenol.

1.8 s-Triazine compounds, such as, for example 2,4-bis-octylmercapto-6-(3,5-di-tert.-butyl-4-hydroxy-anilino)-s-triazine, 2-octylmercapto-4,6-bis-(3,5-di-tert.butyl-4-hydroxy anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert-butyl-4-hydroxyphenylethyl)-s-triazine and 1,3,5-tris-(3,5-di-tert.-butyl-4-hydroxybenzyl)isocyanurate.

1.9 Amides of β-(3,5-di-tert.-butyl-4-hydroxyphenyl)-propionic acid, such as, for example, 1,3,5-tris-(3,5,-ditert.-butyl-4-hydroxyphenyl-propionyl)-hexahydro-s-triazine and N,N'-di-3,5-ditert.-butyl-4-hydroxyphenyl-propionyl)-hexamethylenediamine, N,N'-bis-β-(3,5-di-t-butyl-4-hydroxyphenyl)-propionyl-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thiaundecanol, 3-thia-pentadecanol, trimethylhexnediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methylphenylpropionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thio-diethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]-octane especially the tetrakis ester of pentaerythritol.

1.13 Benzylphosphonates, such as, for example, dimethyl 3,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Metal deactivators, e.g., oxanilide, isophthalic acid dihydrazide, sebacic acid-bis-phenylhydrazide, bis-benzylideneoxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2-4-triazole or N,N'-bis-salicyloyl-thiopropionic acid dihydrazide.

Other additives that can be incorporated in the stabilized compositions are thiosynergists such as dilauryl thiodiproprionate, basic co-stabilizers, nucleation agents, phosphites, phosphonites, lubricants such as stearyl alcohol, fillers, asbestos, kaolin, talc, glass fibers, pigments, optical brighteners, flameproofing agents and antistatic agents. Among this group, phosphites in combination with a blend of UV absorber and piperidine compound are of particular interest.

As previously noted, the fungicides can be effectively stabilized whether they are applied in solution, emulsion or some other liquid form, or whether they are formulated into finished formulations such as paints, lacquers, stains, enamels, substrate treatments such as wood preservatives and water repellent systems, or other coating formulations. Ingredients present in such formulations are well known to those skilled in the art. A number of these ingredients have been listed hereinabove. Additional ingredients include resin systems such as alkyd resins, acrylic resins, polyesters, phenolics, polyurethanes, epoxies and blends thereof; solvents; surfactants; defoamers; thickeners such as carboxymethyl cellulose, polyacrylic or polymethacrylic acids; plasticizers, dispersants; binders; water repellents; oxidizable oils such as vegetable oils; and the like. Pigments and fillers in these formulations function as UV screening agents.

The fungicidal compositions can be applied to a large variety of substrates. Of particular importance is the application of the stabilized fungicide systems to wood, metal or natural or synthetic polymeric substrates for the prevention of mildew and other fungus formations. Textile and paper substrates are likewise applicable. In this manner, the stabilizers prevent the decomposition of the fungicide, thereby facilitating the desired fungicidal activity and providing maximum protection to the substrate.

The following examples further illustrate the embodiments of this invention. In these examples, all parts given are by weight unless otherwise specified.

The following stabilizers are utilized in these examples.

A—2-(2-hydroxy-3,5-di-tert.amylphenyl)-2H-benzotriazole

B—bis(1,2,2,6,6-pentamethyl-4-piperidyl)decanedioate

C—polyester oligomer of 1-(2-hydroxyethyl)-2,2,5,5-tetramethyl-4-hydroxy piperidine and 2,2-diethylmalonic acid D—2-(2-hydroxy-5-methylphenyl)-2H-benzotriazole E—bis(2,2,6,6-tetramethyl-4-piperidyl)sebacate F—bis(1,2,2,6,6-pentamethyl-4-piperidyl)[[3,5-bis(1,1-dimethylethyl-4-hydroxyphenyl)methyl]butyl]-propanedioate G—mixture of 3-(5-chloro-2H-benzotriazole-2-yl)-4-hydroxy-5-(1,1-dimethyl-ethyl phenyl propionic acid)-octyl and -2-ethylhexyl esters H—8-acetyl-3-dodecyl-7,7,9,9-tetramethyl-1,3,8-triazaspiro[4.5]decane-2,4-dione I—2-dodecyl-2'-ethoxy-oxanilide J—2-hydroxy-4-n-octoxybenzophenone K—2,2'-dihydroxy-4-methoxybenzophenone L—2,4-dihydrobenzophenone

EXAMPLE 1

This example illustrates the fungicidal stabilizing capability of the stabilizing system of this invention. In each instance, the effectiveness of light stabilization of the fungicide was determined as the ability to prevent mildew defacement of the coating surface as a function of time.

Outdoor exposure tests were conducted utilizing a linseed oil white stain and wood preservative based on mineral spirits, titanium dioxide pigment, linseed oil and coalescing solvent (2,2,4-trimethyl-1,3-pentanediol monoisobutyrate). Samples were prepared utilizing 0.25%, 0.5%, 1.0%, 2.0% and 2.5%, by weight of the stain, of the following fungicides:

3-iodo-2-propynyl butyl carbamate (Polyphase from Troy Chemical Co.)

1,2-bis(n-propylsulfonyl)ethane (Vancide PA from Vanderbilt Co.)

N-trichloromethylthio-phthalimide (Fungitrol 11 from Tenneco).

In turn, the samples were left unstabilized or stabilized with 1.0% stabilizer A, 1.0% stabilizer B, 1.0% stabilizer A plus 1.0% stabilizer B, and 2.0% stabilizer A plus 1.0% stabilizer B, the percentages being based on the weight of resin solids.

Each formulation was coated onto 1"×8"×12" white pine boards. The boards were cut in half, with one panel being posed outdoors at a position angle of 90°N and the mate thereof being exposed at a position angle of 45°S.

Within four months of exposure, all of the controls exposed at 45°S were severely mildewed. The controls were the stain formulations without fungicide and the stain formulations without fungicide, but with light stabilizers. The failure of the latter control group was significant inasmuch as it demonstrated the lack of fungicidal activity on the part of the stabilizer system. Accordingly, increased fungicidal activity can be attributed solely to the stabilizing effect on the fungicide.

Other results of this testing procedure indicated that a 1% Polyphase formulation stabilized with 1% stabilizer A and 1% stabilizer B decidedly outperformed the unstabilized 1% Polyphase formulation and was equal to or slightly better than the unstabilized 2% Polyphase formulation.

The following test data reflect on certain of these results. Mildew ratings were noted according to ASTM D-3274-76 on a scale of 1–10, with a rating of 10 indicating a mildew-free surface.

| Fungicide Conc. | (%) Stabilizer Conc. | Mildew Rating (at 45° S) | | |
|---|---|---|---|---|
| | | 4 mos. | 6 mos. | 12 mos |
| Vancide PA | | | | |
| 0.5 | — | 8 | 4 | 5 |
| 0.5 | 1.0% stab. B | 9 | 9 | 9 |
| 0.5 | 1.0% stab. A | 9 | 8 | 6 |
| 0.5 | 2.0% stab. A/1.0% stab. B | 8.5 | 9 | 9 |
| 0.5 | 1.0% stab. A/1.0% stab. B | 9 | 8 | 9 |
| 2.0 | — | 9.5 | 9 | 7 |
| Polyphase | | | | |
| 0.5 | — | 6 | 2 | 4 |
| 0.5 | 1.0% stab. B | 8.5 | 7 | 7 |
| 0.5 | 1.0% stab. A | 8 | 8 | 8 |
| 0.5 | 2.0% stab. A/1.0% stab. B | 8 | 8 | 8 |
| 0.5 | 1.0% stab. A/1.0% stab. B | 8 | 6 | 6 |
| 2.0 | — | 9 | 8 | 8 |
| Fungitrol-11 | | | | |
| 0.5 | — | 8 | 8 | 8 |
| 0.5 | 1.0% stab. B | 9 | 8 | 9 |
| 0.5 | 1.0% stab. A | 8 | 6 | 4 |
| 0.5 | 2.0% stab. A/1.0% stab. B | 9 | 9 | 9 |
| 0.5 | 1.0% stab. A/1.0% stab. B | 9 | 9 | 9 |
| 2.0 | — | 9 | 9 | 9 |

The stabilizing effectiveness of the instant stabilizing systems is thus clearly indicated.

EXAMPLE 2

This example further illustrates the fungicidal stabilizing capability of the stabilizing systems of this invention.

The active material utilized in this example was 3-iodo-2-propynyl butyl carbamate (Polyphase), a material utilized as a mildewcide and fungicide. The carbamate was formulated into a clear acrylic emulsion of 60% solids (Rohm & Haas acrylic latex AC-64) at a 1.0%, by weight, active carbamate concentration and appropriate amounts of stabilizer were blended into the emulsion. Films of 90 micron thickness were prepared from the unstabilized emulsion as well as from the various stabilized emulsions. The resulting dry films were then exposed to a fluorescent sunlight/black light chamber for a period of 12 hours and the yellowness index determined by means of ASTM D-1925-63-T.

The stabilizer concentrations (% by weight of resin solids) and the test results are noted in the following table.

| Stabilizer System % | | | |
|---|---|---|---|
| A | B | C | Yellowness Index |
| Control | | | 38.87 |
| 1.5 | 1.5 | — | 19.76 |
| 1.5 | 1.0 | — | 19.32 |
| 1.5 | 0.5 | — | 19.00 |
| 0.5 | 1.0 | — | 27.98 |
| 0.5 | 0.5 | — | 28.35 |
| 0.5 | 1.5 | — | 30.82 |
| 0.5 | — | — | 31.11 |
| 1.0 | — | — | 24.77 |
| 1.5 | — | — | 23.21 |
| — | 0.5 | — | 41.19 |
| — | 1.0 | — | 45.63 |
| — | 1.5 | — | 45.59 |
| 1.0 | 1.0 | — | 25.00 |
| 1.0 | 1.5 | — | 23.33 |
| 1.0 | 0.5 | — | 24.53 |
| 1.0 | — | 1.0 | 27.05 |
| — | — | 1.0 | 19.00 |

Since the breakdown products of Polyphase are yellow, these results clearly indicate the biocide stabilization characteristics of the instant systems. In reviewing this data, it should be recognized that accelerated weathering devices employing UV energy may not be the preferred vehicle for determining the stabilization activity of stabilization systems containing only the piperidine compounds. Rather, such results should be considered in combination with other test data to obtain a true performance profile

EXAMPLE 3

The photodecomposition characteristics of the carbamate of Example 1 were furthered studied by means of thin layer chromatography Thus the carbamate 1 part of the carbamate combined with 2 parts of stabilizer D, 1 part of the carbamate with 2 parts of stabilizer E and 1 part of the carbamate combined with a blend of 2 parts stabilizer D and 2 parts stabilizer E were subjected to a low pressure mercury vapor lamp for a period of 15 minutes and then tested by chromatography in methylene chloride solvent to determine the existence of decomposition product. The chromatographic study indicated that the stabilized carbamate after exposure exhibited the same pattern as the unexposed carbamate, with the unstabilized, exposed carbamate showing distinct evidence of decomposition.

EXAMPLE 4

The following solution study under UV irradiation was conducted in order to determine the amount of residual Nopcocide N96 (tetrachloro isophthalonitrile—a broad spectrum mildewcide from Diamond Shamrock Corp.) in solution after periods of UV exposure. A control sample was prepared containing 20 mg. of Nopcocide in 1000 ml. of toluene. The stabilized samples contained 20 mg. of Nopcocide and 75 mg. of stabilizer in 1000 ml. of toluene. The control and stabilized samples were exposed in a fluorescent sunlight-black light chamber in sealed vials for a period in excess of 105 minutes. The residual Nopcocide was determined by gas chromatography. The results are noted below:

| Sample | Conc. (mg) | % Residual Fungicide after | | | | |
|---|---|---|---|---|---|---|
| | | 0 min. | 15 min. | 30 min. | 45 min. | 60 min. |
| Control | — | 100 | 30.0 | 7.0 | 4.0 | 0.5 |
| Stab. A | 75 | 100 | 97.0 | 100.0 | 85.5 | 86.0 |
| Stab. C | 75 | 100 | 44.5 | 18.0 | 4.5 | 2.5 |
| Stab. A + Stab. C | 75 75 | 100 | 94.0 | 86.5 | 84.0 | 84.0 |

These data clearly establish the stabilizing effectiveness of the stabilizers of this example in terms of maintaining the active ingredient.

EXAMPLE 5

Films of 120 micron thickness were prepared from (1) AC-64 acrylic latex (60% solids); (2) AC-64 and 1% by weight of Nopcocide N96; and (3) AC-64, 1% of N96, 1% of stabilizer A and 1% of stabilizer B, the latter percentages being based on resin solids. Each of the films was subjected to UV irradiation. Film 1 was seen to be UV transparent, i.e. limited visibility. Film 2 was highlighted due to the fluorescent effect on the N96. This fluorescent effect suggests that the N96 is absorbing UV light energy. Since the mildewcide in the fluorescent state is in an excited state, decomposition can be anticipated.

In contrast, the stabilized film was dark due to the absorption of the ultraviolet light by the stabilizer system. Decomposition would not be anticipated in the latter instance.

EXAMPLE 6

This example illustrates the stabilizing effectiveness of the instant system when incorporated into a fungicide-containing, standard latex white house paint.

The following paint formulation was utilized.

|  | Parts |
| --- | --- |
| water | 100.0 |
| defoamer | 0.5 |
| ethylene glycol | 14.0 |
| hydroxyethyl cellulose | 1.0 |
| surfactant | 6.75 |
| titanium dioxide | 125.0 |
| talc | 100.0 |
| acrylic latex (AC-64) | 182.0 |
| defoamer | 0.5 |
| fungicide (Polyphase) | 6.0 |
| coalescing solvent* | 58.0 |
| water | 10.0 |

*2,2,4-trimethyl-1,3-pentanediol monoisobutyrate

A second sample of the paint was prepared in identical fashion with the exception that the acrylic latex was blended with 1% stabilizer A and 1% stabilizer B (each based on weight of solids) prior to its addition to the formulation.

Each paint was then applied to strips of cellulosic filter paper, dried and exposed in the fluorescent sunlight/black light chamber for a period of 12 hours. The change in yellowness index (YI) was then determined by ASTM D-1925-63-T, with the samples before exposure exhibiting a YI of 3, the exposed control exhibiting a YI of 41.1 and the exposed stabilized system exhibiting a YI of 16.22. Accordingly, it was noted that the stabilized paint layer was far more attractive than the yellowed unstabilized system.

EXAMPLE 7

A commercial exterior oil-based alkyd paint (Sears Semi-Gloss Trim) containing 0.5% 2,3,5,6-tetrachloro-4-(methylsulfonyl)-pyridine mildewcide (Dowicil S13 from Dow Chemical Corp.) and a similar paint containing 1% of stabilizer A and 1% of stabilizer B (based on resin solids) were applied to Bonderite 1000 cold rolled steel panels and the panels exposed at an angle of 45°S for one year in southern Florida. An inspection of the panels revealed a substantial amount of mildew growth on the control panel as contrasted with a minimal amount of mildew formation of the panel painted with the stabilized formulation. It is clear, therefore, that the light stabilizers have maintained the effectiveness of the mildewcide by protecting it from UV induced decomposition.

Scanning electron micrographs of the respective coatings revealed that the stabilized coating had a less extensive and less dense growth of hyphae (mildew fungi) than the unstabilized coating. These observations further confirm the retention of a toxic environment in the stabilized system.

EXAMPLE 8

A procedure similar to that of Example 4 was utilized to determine the amount of residual pentachlorophenol, a widely recognized fungicide and mildewcide, after periods of UV exposure.

Solutions of 20 ppm pentachlorophenol in toluene were prepared. Control samples were retained while other samples were formulated containing 80 ppm stabilizer A, 80 ppm stabilizer F and a blend of 80 ppm stabilizer A and 80 ppm stabilizer F, respectively. The control and stabilized samples were exposed in the fluorescent sunlight/black light chamber for varying intervals of time.

The basic method utilized for analysis of pentachlorophenol is described in Satoh, "Photochemical Reaction of Chlorothalonil in Organic Solvents, "Bull. Environ. Contam. Tox. 22, 590–597 (1979). This procedure required derivitization of the pentachlorophenol by the procedure described on page 179 of the 1982-83 Pierce Products Catalog [Kawahara, Anal. Chem., 40, No. 6, 1009 (1968)]. The results of these evaluations are noted in the following table.

|  | Con- | Residual Pentachlorophenol (%) | | |
| --- | --- | --- | --- | --- |
| Exposure Time (min) | trol | Stab. A | Stab F | Stab A + F |
| 0 | 100 | 100 | 100 | 100 |
| 10 | 67 | 100 | 69.82 | 100 |
| 15 | 56.18 | 100 | 58.88 | 97.08 |
| 30 | 30.77 | 98.7 | 34.04 | 96.08 |
| 45 | 16.04 | 91.5 | 20.96 | 94.94 |
| 60 | 5.9 | 93.33 | 12.26 | 85.14 |

This data further confirms the stabilizing effectiveness of the instant systems in terms of preventing decomposition of active material.

EXAMPLE 9

A 15%, by weight, toluene solution of a thermoplastic acrylic ester resin (Acryloid B-66 from Rohm & Haas) was prepared and 10 grams thereof were blended with 0.1 gram of pentachlorophenol and approximately 0.5 grams of total stabilizer. Thereafter, 1.0 gram of the formulation was roll coated into a thin film on the interior wall of a vial and dried by evaporation. The vial was capped and exposed in the fluorescent sunlight/black light chamber for the indicated exposure time. Following exposure, each sample was extracted and analyzed for residual pentachlorophenol by the procedure of Example 8 utilizing gas chromatographic analysis with an electron capture detector.

The results are noted in the following table.

|  |  | % Retention after | | |
| --- | --- | --- | --- | --- |
| Stabilizer | Conc. (%) | 0 hrs. | 24 hrs. | 65 hrs. |
| Control | — | 100.0 | 16.0 | 5.0 |
| F | 5 | 100.0 | 100.0 | 100.0 |
| G | 5 | 100.0 | 100.0 | 100.0 |
| H | 5 | 100.0 | 34.0 | 21.0 |
| F + G | 2.5 + 2.5 | 100.0 | 100.0 | 100.0 |
| G + H | 2.5 + 2.5 | 100.0 | 100.0 | 100.0 |
| G + H | 1.6 + 1.6 | 100.0 | 100.0 | 100.0 |
| +Antioxidant* | + 1.6 |  |  |  |

*Thiodiethylene bis-(3,5-di-tert-butyl-4-hydroxy)hydrocinnamate

The test procedure thus further demonstrated the ability of the instant stabilizer systems to maintain the integrity of fungicides.

EXAMPLE 10

The procedure of Example 9 was repeated to prepare the films in the capped vials. Following exposure, 10 mls. of chloroform were introduced into each vial to extract the film. A 5 ml. aliquot of the extract was further diluted in 10.0 ml. of chloroform and a thin layer chromatograph performed on pre-coated silica gel plates utilizing ultraviolet fluorescence as the detecting mechanism. The solvent systems utilized for the different fungicides for TLC development were as follows.

| Fungicide | Solvent |
| --- | --- |
| Nopcocide N-96 | methylene chloride |
| Fungitrol-11 | 70:30 benzene/n-hexane |
| pentachlorophenol | methylene chloride |
| Amical 48* | methylene chloride |
| Skane M-8** | 90:10 methylene chloride/methanol |

*diiodomethyl paratolyl sulfone from Abbott Laboratories
**2-n-octyl-4-isothiazolin-3-one from Rohm & Haas Corp.

The results are noted in the following table:

| Fungicide System | Exposure Time (hrs.) | $R_f$ Value* | Comment |
| --- | --- | --- | --- |
| Nopcocide N-96 | | | |
| control | 0 | .58 | standard $R_f$ |
| control | ~200 | .58 | decreased spot intensity |
| +5% Stab. A | ~200 | .58 | standard $R_f$ |
| +5% Stab. H | ~200 | .58 | slightly decreased spot intensity |
| Fungitrol-11 | | | |
| control | 0 | .15 | standard $R_f$ |
| control | ~200 | — | spot not observed |
| +5% Stab. B | ~200 | — | spot not observed |
| +5% Stab. G | ~200 | .15 | standard $R_f$ |
| { +5% Stab. B | ~200 | — | spot not observed |
|   +5% Stab. G | | | |
| Amical 48 | | | |
| control | 0 | .40 | standard $R_f$ |
| control | 64.0 | — | spot not observed |
| +5% Stab. F | 64.0 | .40 | standard $R_f$ |
| +5% Stab. I | 64.0 | .40 | standard $R_f$ |
| Skane M8 | | | |
| control | 0 | .6 | standard $R_f$ |
| control | 64.0 | — | spot not observed |
| +5% Stab. J | 64.0 | .6 | standard $R_f$ |
| { +5% Stab. J | 64.0 | .6 | standard $R_f$ |
|   +5% Stab. C | | | |
| pentachlorophenol | | | |
| control | 0 | 0.30 | standard $R_f$ |
| control | 64.3 | — | spot not observed |
| +5% Stab. E | 64.3 | — | spot not observed |
| { +5% Stab. H | 64.3 | 0.30 | standard $R_f$ |
|   +5% Stab. G | | | |

*$R_f$ value indicates the differential between the chromatographic distance travelled by the solvent and the distance traveled by the active ingredient.

This test model also demonstrates the ability of UV absorbers and piperidine compounds to protect fungicides from photo-oxidation.

EXAMPLE 11

The procedure of Example 1 was repeated utilizing a terpene clear wood finish and a linseed oil clear wood finish, each containing 1%, by weight of phenyl mercuric oleate mildewcide. The panels which contained both stabilized and unstabilized areas, were exposed outdoors at a position angle of 45° S. Mildew ratings were again noted according to ASTM D-3274-76 on a scale of 1-10, with a rating of 10 reflecting a mildew-free surface.

The following stabilizer systems were utilized

| Stabilizer | Conc. (%) |
| --- | --- |
| A | 2 |
| A | 4 |
| B | 1 |
| B | 2 |
| A + B | 2 + 1 |
| A + B | 4 + 2 |
| K | 2 |
| K | 4 |
| L | 2 |
| L | 4 |

All panels exhibited a mildew free surface at the initiation of the test procedure. After a five month exposure period, virtually all of the unstabilized areas showed mildew formation. Mildew ratings for the latter areas ranged from 3–9. In contrast, each of the stabilized areas had a mildew rating of 10 after the five month period indicating a mildew-free surface and effective stabilization of the mildewcide.

In summary, this invention provides novel stabilized fungicide systems which exhibit excellent performance characteristics. Variations may be made in procedures, proportions and materials without departing from the scope of the invention as defined by the following claims.

What is claimed is:

1. A composition of matter comprising a fungicide subject to light-induced deterioration stabilized with an effective stabilizing amount of a 2,2,6,6-tetraalkylpiperidine compound.

2. The composition of matter of claim 1, wherein said compound contains a group of the formula

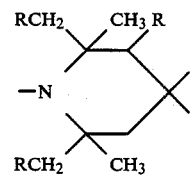

wherein R is hydrogen or methyl.

3. The composition of claim 2, wherein R is hydrogen.

4. A composition of matter comprising a fungicide subject to light-induced deterioration stabilized with an effective light stabilizing amount of a blend of a 2,2,6,6-tetraalkylpiperidine compound and a UV absorber.

5. The composition of claim 4, wherein said piperidine compound and said UV absorber being present in relative concentrations of 16:1 to 1:16.

6. The composition of claim 1, wherein said 2,2,6,6-tetraalkylpiperidine compound corresponds to the formula (II)

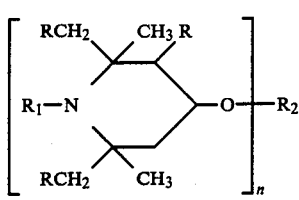

(II)

in which n is a number from 1–4 inclusive; R is hydrogen or methyl; $R_1$ is hydrogen, oxyl, $C_1$–$C_{18}$ alkyl, $C_3$–$C_8$ alkenyl, $C_1$–$C_8$ alkynyl, $C_7$–$C_{12}$ aralkyl, $C_1$–$C_8$ alkanoyl, $C_3$–$C_5$ alkenoyl, glycidyl or a group —CH$_2$—CH(OH)—Z wherein Z is hydrogen, methyl or phenyl, and $R_2$ when n is 1 is hydrogen, $C_1$–$C_{18}$ alkyl optionally interrupted by one or more oxygen atoms, cyanoethyl, benzyl, glycidyl, a monovalent radical of an aliphatic, cycloaliphatic, araliphatic or aromatic carboxylic acid, or of carbamic acid or of a phosphorus-containing acid, or a monovalent silyl radical; $R_2$ when n is 2 is $C_2$–$C_{12}$ alkylene, $C_4$–$C_{12}$ alkenylene, xylylene, a bivalent radical of an aliphatic, cycloaliphatic, araliphatic or aromatic dicarboxylic acid, of dicarbamic acid or of a phosphorus-containing acid, or a bivalent silyl radical; $R_2$ when n is 3 is a trivalent radical of an aliphatic, cycloaliphatic or aromatic tricarboxylic acid, of an aromatic tricarbamic acid or of a phosphorus-containing acid, or a trivalent silyl radical; and $R_2$ when n is 4 is a tetravalent radical of an aliphatic, cycloaliphatic or aromatic tetracarboxylic acid.

7. The composition of claim 4, wherein said 2,2,6,6-tetraalkyl piperidine compound corresponds to the formula II

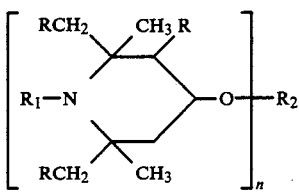

(II)

in which n is a number from 1–4 inclusive; R is hydrogen or methyl; $R_1$ is hydrogen, oxyl, $C_1$–$C_{18}$ alkyl, $C_3$–$C_8$ alkenyl, $C_1$–$C_8$ alkynyl, $C_7$–$C_{12}$ aralkyl, $C_1$–$C_8$ alkanoyl, $C_3$–$C_5$ alkenoyl, glycidyl or a group —CH$_2$—CH(OH)—Z wherein Z is hydrogen, methyl or phenyl; and $R_2$ when n is 1 is hydrogen, $C_1$–$C_{18}$ alkyl optionally interrupted by one or more oxygen atoms, cyanoethyl, benzyl, glycidyl, a monovalent radical of an aliphatic, cycloaliphatic, araliphatic or aromatic carboxylic acid, or of carbamic acid or of a phosphorus-containing acid, or a monovalent silyl radical; $R_2$ when n is 2 is $C_2$–$C_{12}$ alkylene, $C_4$–$C_{12}$ alkenylene, xylylene, a bivalent radical of an aliphatic, cycloaliphatic, araliphatic or aromatic dicarboxylic acid, of dicarbamic acid or of a phosphorus-containing acid, or a bivalent silyl radical; $R_2$ when n is 3 is a trivalent radical of an aliphatic, cycloaliphatic or aromatic tricarboxylic acid, of an aromatic tricarbamic acid or of a phosphorus-containing acid, or a trivalent silyl radical; and $R_2$ when n is 4 is a tetravalent radical of an aliphatic, cycloaliphatic or aromatic tetracarboxylic acid.

8. A composition according to claim 6, wherein in the stabilizer of formula (II)

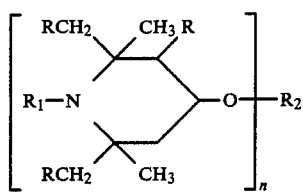

(II)

n is the number 1 or 2; R is hydrogen or methyl; $R_1$ is hydrogen, $C_1$–$C_{12}$ alkyl, allyl, benzyl, acetyl or acryloyl; and $R_2$, when n is 1, is a radical of an aliphatic carboxylic acid having 2–18 C atoms, of a cycloaliphatic carboxylic acid having 5–12 C atoms or of an aromatic carboxylic acid having 7–15 C atoms; and $R_2$, when n is 2, is a radical of an aliphatic dicarboxylic acid having 2–36 C atoms, of a cycloaliphatic or aromatic dicarboxylic acid having 8–14 C atoms or of an aliphatic, cycloaliphatic or aromatic dicarbamic acid having 8–14 C atoms.

9. A composition according to claim 7, wherein in the stabilizer of formula (II)

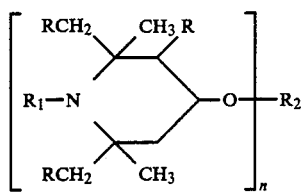

(II)

n is the number 1 or 2; R is hydrogen or methyl $R_1$ is hydrogen, $C_1$–$C_{12}$ alkyl, allyl, benzyl, acetyl or acryloyl; and $R_2$, when n is 1, is a radical of an aliphatic carboxylic acid having 2–18 C atoms, of a cycloaliphatic carboxylic acid having 5–12 C atoms or of an aromatic carboxylic acid having 7–15 C atoms; and $R_2$, when n is 2, is a radical of an aliphatic dicarboxylic acid having 2–36 C atoms, of a cycloaliphatic or aromatic dicarboxylic acid having 8–14 C atoms, or of an aliphatic, cycloaliphatic or aromatic dicarbamic acid having 8–14 C atoms.

10. A composition according to claim 1, wherein said piperidine compound is bis-(2,2,6,6-tetramethyl-4-piperidyl) sebacate.

11. A composition according to claim 4, wherein said piperidine compound is bis-(2,2,6,6-tetramethyl-4-piperidyl) sebacate.

12. A composition according to claim 1, wherein said piperidine compound is bis(1,2,2,6,6-pentamethyl-4-piperidyl) decanedioate.

13. A composition according to claim 4, wherein said piperidine compound is bis(1,2,2,6,6-pentamethyl-4-piperidyl decanedioate.

14. The composition according to claim 1, wherein said piperidine compound is the polyester oligomer of 1-(2-hydroxyethyl)-2,2,6,6-tetramethyl-4-hydroxypiperidine and 2,2-diethylmalonic acid; bis (1,2,2,6,6-pentamethyl-4-piperidyl)[[3,5-bis(1,1-di-methylethyl-4-hydroxyphenyl)methyl]butyl]propanedioate or the mixture of 3-(5-chloro-2H-benzotriazole-2-yl)-4-hydroxy-5-(1,1-dimethylethyl-phenylpropionic acid)-octyl- and -2-ethylhexyl esters.

15. The composition according to claim 4, where said piperidine compound is the polyester oligomer of 1-(2-hydroxyethyl)-2,2,6,6-tetramethyl-4-hydroxypiperidine and 2,2-diethylmalonic acid; bis (1,2,2,6,6-pentamethyl-4-piperidyl) [[3,5-bis(1,1-di-methylethyl-4-hydroxyphenyl)methyl]butyl]propanedioate; or the mixture of 3-(5-chloro-2H-benzotriazole-2-yl)-4-hydroxy-5-(1,1-dimethylethyl-phenylpropionic acid)-octyl- and -2-ethylhexyl esters.

16. The composition of claim 4, wherein said U.V. absorber is selected from the group consisting of 2-(2-hydroxyphenyl)-2H-benzotriazoles, 2,4-bis(2-hydroxyphenyl)-6-alkyl-s-triazines, 2-hydroxybenzophenones, 1,3-bis(2-hydroxybenzoyl)-benzenes, esters of benzoic acids, acrylates and oxalic acid diamides.

17. The composition of claim 16, wherein said U.V. absorber is a benzotriazole.

18. The composition of claim 17, wherein said benzotriazole is 2-(2-hydroxy-4-methylphenyl)-2H-benzotriazole or 2-(2-hydroxy-3,5-di-tert.amylphenyl)-2H-benzotriazole.

19. The composition of claim 16, wherein said U.V. absorber is 8-acetyl-3-dodecyl-7,7,9,9-tetramethyl-1,3,8-triazaspiro[4.5]decane-2 4-dione 2-dodecyl-2'-ethoxyoxanilide 2-hydroxy-4-n-octoxybenzophenone; 2,2'-dihydroxy-4-methoxybenzophenone or 2,4-dihydroxybenzophenone.

20. The composition of claim 4, wherein said stabilizer is a blend of bis(1,2,2,6 6-pentamethyl-4-piperidinyl)decanedioate and 2-(2-hydroxy-3,5-di-tert.amylphenyl)-2H-benzotriazole.

21. The composition of claim 1, wherein said fungicide is selected from the group consisting of carbamates arsenic compounds, chlorinated phenols, copper compounds, chlorinated compounds other than chlorinated phenols organo mercury compounds, organic tin compounds, zinc compounds, ketones, sulfonyl compounds and azole compounds.

22. The composition of claim 4, where said fungicide is selected from the group consisting of carbamates, arsenic compounds, chlorinated phenols copper compounds chlorinated compounds other than chlorinated phenols, organo mercury compounds organic tin compounds, zinc compounds ketones, sulfonyl compounds and azole compounds.

23. The composition of claim 1, which is present in a paint lacquer stain enamel, substrate treatment or other coating formulation.

24. The composition of claim 4, which is present in a paint lacquer stain enamel substrate treatment formulation or other coating formulation.

25. The method of stabilizing fungicides against light-induced deterioration which comprises adding to said fungicide an effective stabilizing amount of a stabilizing composition according to claim 1.

26. A method of stabilizing fungicides against light-induced deterioration which comprises adding to said fungicide an effective stabilizing amount of a stabilizing composition according to claim 4.

* * * * *